(12) United States Patent
Boschetti Sacco et al.

(10) Patent No.: US 9,138,150 B2
(45) Date of Patent: Sep. 22, 2015

(54) PORTABLE PULSEOXIMETER FOR A DIRECT AND IMMEDIATE AUTOMATED EVALUATION OF THE CARDIAC RHYTHM (REGULARITY) AND RELATED METHOD

(75) Inventors: Paolo Boschetti Sacco, Rome (IT); Pietro Bartolini, Rome (IT); Giovanni Calcagnini, Rome (IT); Federica Censi, Rome (IT); Eugenio Mattei, Rome (IT); Michele Triventi, Foggia (IT)

(73) Assignee: MIR SRL-MEDICAL INTERNATIONAL RESEARCH, Rome (IT)

( * ) Notice: Subject to any disclaimer, the term of this patent is extended or adjusted under 35 U.S.C. 154(b) by 404 days.

(21) Appl. No.: 13/805,803

(22) PCT Filed: Jul. 2, 2010

(86) PCT No.: PCT/IT2010/000299
§ 371 (c)(1),
(2), (4) Date: Dec. 20, 2012

(87) PCT Pub. No.: WO2012/001719
PCT Pub. Date: Jan. 5, 2012

(65) Prior Publication Data
US 2013/0102864 A1    Apr. 25, 2013

(51) Int. Cl.
A61B 5/0205    (2006.01)
A61B 5/024     (2006.01)
A61B 5/1455    (2006.01)
A61B 5/00      (2006.01)

(52) U.S. Cl.
CPC .......... *A61B 5/0205* (2013.01); *A61B 5/02416* (2013.01); *A61B 5/14551* (2013.01); *A61B 5/7225* (2013.01); *A61B 5/7264* (2013.01); *A61B 5/7278* (2013.01); *A61B 5/7282* (2013.01); *A61B 5/1455* (2013.01); *A61B 5/6826* (2013.01); *A61B 5/7203* (2013.01); *A61B 5/7221* (2013.01)

(58) Field of Classification Search
CPC ............ A61B 5/0205; A61B 5/02416; A61B 5/1455; A61B 5/14551; A61B 5/6826; A61B 5/7203; A61B 5/7221; A61B 5/7225; A61B 5/7264; A61B 5/7278; A61B 5/7282
See application file for complete search history.

*Primary Examiner* — Rex R Holmes
(74) *Attorney, Agent, or Firm* — Young & Thompson

(57) ABSTRACT

A method and system of patient monitoring, the system performs short term acquisition of the plethysmographic waveform of a patient from a portable blood oxygenation level monitoring device and establishes whether the patient has an episode of Atrial Fibrillation (AF) or has a Normal Sinus Rhythm (NSR) or any other not-specific rhythm irregularity. Such classification is implemented directly in the device, suitable for at home use, and the result of the classification is displayed automatically using a three-state, traffic-light indicator.

11 Claims, 2 Drawing Sheets

PORTABLE PULSEOXIMETER FOR A DIRECT AND IMMEDIATE AUTOMATED EVALUATION OF THE CARDIAC RHYTHM (REGULARITY) AND RELATED METHOD

The present invention relates to the field of patient monitoring. More particularly the invention relates to a system that performs short term acquisition of the plethysmographic waveform of a patient from a portable blood oxygenation level monitoring device and establishes whether the patient has an episode of Atrial Fibrillation (AF) or has a Normal Sinus Rhythm (NSR) or any other not-specific rhythm irregularity. Such classification is implemented directly in the device, suitable for at home use, and the result of the classification is displayed automatically using a three-state, traffic-light indicator.

BACKGROUND OF THE INVENTION

Atrial Fibrillation Epidemiology

Atrial fibrillation is the most common sustained cardiac arrhythmia and affects more than 2 million individuals in the USA. Prevalence is expected to rise substantially over the next few decades because of the ageing population, improved cardiovascular treatments, and lengthened survival of individuals with heart disease. This condition is associated with strikingly increased morbidity and mortality. The most life-threatening consequences of atrial fibrillation are thromboembolic events and heart failure.

Importance of AF Diagnosis

Early identification of individuals who are at risk in the community would allow prevention and targeted intervention, and could decrease health-care costs. Also, once diagnosed, the arrhythmia can recur even under drug therapy, and the detection of arrhythmia recurrences can help in optimizing therapy. The results from AFFIRM study demonstrated a higher incidence of stroke (57%) in the "rhythm control" group after anticoagulation discontinuation despite the detection of sinus rhythm in an ambulatory ECG [1]. This result underlines how critical is the choice of a therapy for paroxymal AF and how difficult the choice becomes when the feedback about the patient status is based on symptoms and/or sporadic ECG.

Methods for Atrial Fibrillation Diagnosis

Many patients with AF are identified once they are symptomatic or, fortuitously, when they go to the clinician for an unrelated complaint, and, in the course of the office visit, they have their ECG recorded.

Common methods of atrial arrhythmia monitoring include intermittent 24-hour Halter monitoring, infrequent periods of long-term monitoring (e.g., 7-day or 30-day recordings), and the transient use of event monitors when symptoms are present. However, many studies demonstrated the unreliability of AF diagnosis based on symptoms, because of many reasons including the change of symptom perception after ablation procedures and the influence of drug therapy independently of the heart rate. Indeed, AF is not always accompanied by clear symptoms and symptoms suggestive of AF may not correspond to a genuine AF episode. Previous studies have underscored the unreliability of AF diagnosis based on symptoms in patients. Furthermore, symptom perception may change after procedures such as AF ablation. During AF episodes, symptoms may be correlated to the heart rate (HR) and its irregularity, but drug therapy may also influence symptom perception independently of the HR.

Each diagnosis method presents significant limitations for the diagnosis and quantification of atrial arrhythmias. The ability of Holter monitoring to diagnose and quantify AF is highly dependent on whether or not the day(s) selected for monitoring coincides with a cluster of AF episodes. External recorders now are capable of recording for up to 30 days and have been shown to increase the yield for arrhythmia detection compared with a single 24-hour Holter monitor. However, these external devices often are bulky and interfere with showering and other daily activities. In addition, the patch electrodes can cause skin irritation over such prolonged usage. As a result, patient compliance with such systems often is relatively low.

Daily transmission of short segments of ECG is also available (tele-ECG), but it requires the use of a few number of electrodes, together with a certain degree of patient skill and compliance. Data suggest that the vast majority of AF episodes are asymptomatic and that most symptoms attributed to AF actually are not associated with the arrhythmia. Therefore, monitoring of AF episodes based on only symptomatic events will adversely affect the reliability of identifying patients with AF. Finally, although chronic monitoring with implantable devices has been demonstrated to have both high sensitivity and specificity, this monitoring requires an invasive implant procedure.

Necessity of AF Daily Monitoring

The intermittent nature of AT/AF episodes is diagnostically challenging and inevitably limits the usefulness of the snapshots provided by sporadic ECG monitoring. In addition, delayed information (by 7-day or 30-day Holter) about the onset of atrial fibrillation does not allow an immediate reaction with any therapy: indeed, prompt detection of the onset of AF provides an opportunity for therapy during the first 48 hours when expensive antithrombotic treatments may not be necessary because the formation of blood clots has not yet occurred in the atria. Finally, the longer patients are in AF, the more likely they are to remain in AF, making early detection desirable.

In an exhaustive review analyzing noninvasive methods of continuous cardiac monitoring to detect atrial fibrillation/flutter [2], it has been stated that increased duration of monitoring appears to be associated with increased rates of detection of AT/AF. However, the review was unable to determine the optimal duration of monitoring and the best time to initiate cardiac monitoring, since there are no systematic data on early monitoring (within 48 hours) of AT/AF events. The development of an accurate and specific (sensitive) AT/AF monitoring has become a necessity. Cardiac event recorders or event loop recorders are external devices to be worn for long periods (up to 30-day) and often interfere with some daily activities, besides providing a sporadic monitoring.

From the analysis of the accuracy of several follow-up strategies after AF ablation conducted by Arya et al, [3] it emerges that the method with a degree of accuracy closer to the theoretic gold standard—or to the implantable device—is the daily ECG. Such a strategy can be easily developed by modern technology. In addition, daily ECG detection accuracy could gain benefit by optimizing the time moment of the ECG recording, that is performing a temporally-optimized ECG recording. Such a new concept of monitoring could improve the strategies to follow-up patient even at home and to optimize the therapy.

Home-Daily Monitoring and AF Detection

The possibility of home monitoring of AF episodes relies on two main factors: the feasibility of self recordings of a suitable physiological signal (i.e. a signal containing the information related to the heart rhythm); the availability of a reliable algorithm to analyze such signal.

Automatic detection of AF is achieved by analysis of the electrocardiographic signal. The absence of the P-waves is the main criterium for AF detection. Alternative methods have been proposed. These methods are based on the measure of the irregularity of the ventricular rhythm. Various measures of such irregularity are known [4-10]. These measures quantify the variability of the RR intervals obtained from ECG signals, using combinations of various features: standard deviations and probability density function [4], wavelet transform [5] entropy, Lorenz plots [6], probability density function of an embedded time series [7], Turning point ratio, standard deviation and entropy [8], Markov modeling in combination with P-wave analysis [9], Poincaré plots [10].

It is known that ventricular rhythm can be extracted also from pulseoxymetric waveforms, during normal sinus rhythm [11][12]. The reliability of ventricular rhythm during AF is not known.

It is known that the detection of AF from pulseoxymeter signals can be done by processing the combined information contained in the waveform amplitude and in the inter-beat intervals (US Patent 2007/0255146), using contextual analysis and hidden Markov model. The feasibility of AF detection using only the information carried on by the ventricular rhythm extracted by the pulseoxymetric signal has not been proved.

SUMMARY OF THE INVENTION

The invention consists of a system that performs short term acquisition of the plethysmographic waveform of a patient from a blood oxygenation level monitoring device and establishes whether the patient has an episode of Atrial Fibrillation (AF), or has a Normal Sinus Rhythm (NSR) or any other not-specific rhythm irregularity. Such classification is implemented in a software application that can be executed directly in the device, and the result of the classification is displayed using a three-state, traffic-light indicator.

The plethysmographic waveform is taken from the patient's finger and is processed so that to obtain the pulse interval series.

Artifacts are rejected using a parametric modeling of the pulse waveform contour. Each detected beat is segmented into three sections. The similarity of the first section to a linear segment and the similarity of the third segment to an exponential decay are used to discriminate proper beats from artifacts. Similarity is assessed using the goodness of fit with linear and exponential interpolating functions.

An inter-beat series is obtained calculating the time delay between adjacent beats. Time delays shorter than 0.3 s or longer than 1.5 s are discharged from the further analysis.

This beat-to-beat series (PP intervals) is analyzed and two indexes are extracted, namely the coefficient of variation (CV) and the Shannon entropy (EN).

The combination of these two indexes is used to establish if the patient is in AF or not, by using a measure of the distance of the patient parameters from a reference population. Such distance is calculated using the Mahalanobis formula.

Coefficients and thresholds used for the classification are obtained from reference populations, and are embedded in the system.

The entire algorithm is implemented on an embedded system, preferably directly connected to the pulse oxymeter sensor.

DETAILED DESCRIPTION OF TEE INVENTION

The method for the detection of AF episode is based on the estimation of the heart rhythm irregularity, specifically on two indexes extracted from the beat-to-beat interval series obtained from pulseoximetric waveform.

The method foresees the following steps:
Acquisition of the pulseoximetric signal/waveform from the finger.
Estimation of the time-occurrence of each beat from the pulseoximetric waveform.
Construction of the beat-to-beat series.
Beat validation to reduce artifacts
  Characterization of pulseoximetric waveform, by morphological analysis of the ascendant and descendent tracts of a single pulse
  Removal of beat intervals with values lower than 0.3 s and longer than 1.5 s
Estimation of quantitative indexes
  Coefficient of variation of the first differences of beat-to-beat interval series
  Shannon entropy of the beat-to-beat interval series
Classification of the heart rhythm:
  Estimation of the Mahalanobis distance from population with sinus rhythm and with AF.

Figure 1:
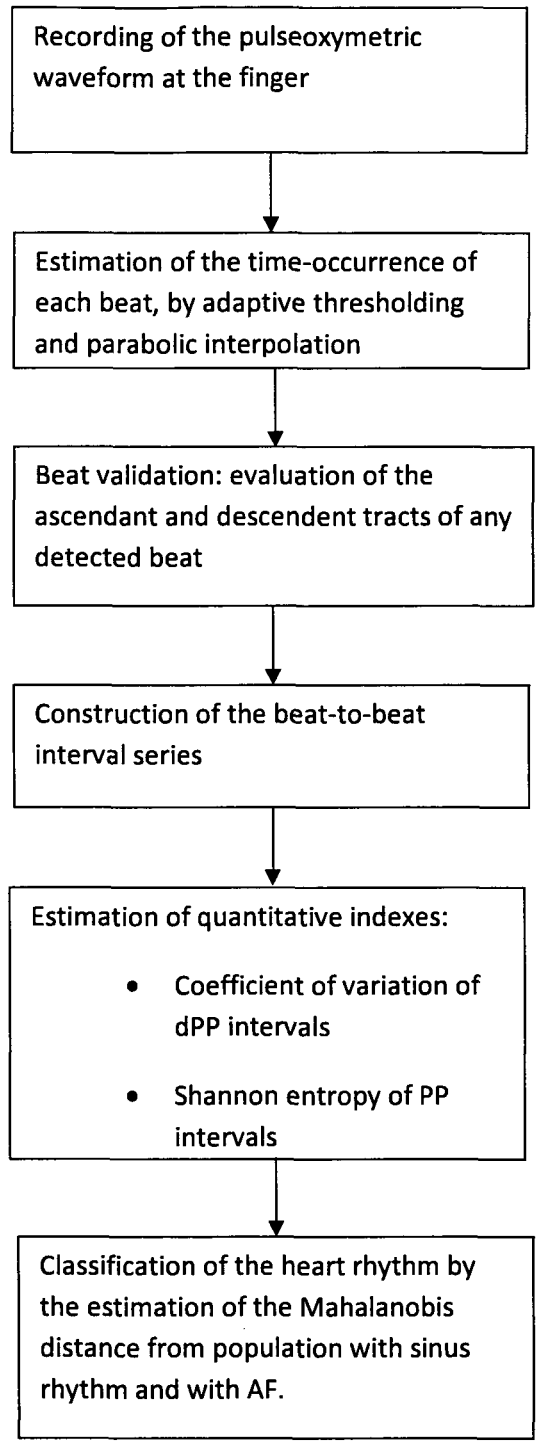
FIG. 1 is a block diagram of the process of the invention.

With reference to FIG. 1, the device according to the present invention substantially carries out a process comprising the following steps:
1. Recording of the pulseoxymetric waveform at the finger;
2. Estimation of the time-occurrence of each beat, by adaptive thresholding and parabolic interpolation;
3. Beat validation: evaluation of the ascendant and descendent tracts of any detected beat;
4. Construction of the beat-to-beat interval series
5. Estimation of quantitative indexes:
   Coefficient of variation of dPP intervals
   Shannon entropy of PP intervals
6. Classification of the heart rhythm by the estimation of the Mahalanobis distance from population with sinus rhythm and with AF.

Details on Beat Validation

Artifacts are rejected using a parametric modeling of the pulse waveform contour. Each detected beat is segmented into three sections. The similarity of the first section to a linear segment and the similarity of the third segment to an exponential decay are used to discriminate proper beats from artifacts. Similarity is assessed using the goodness of fit (R-squared) with linear and exponential interpolating functions. If the R-squared of the linear and exponential tracts are lower than a reference level, the beat is categorized as artifact and neglected.

Figure 2:
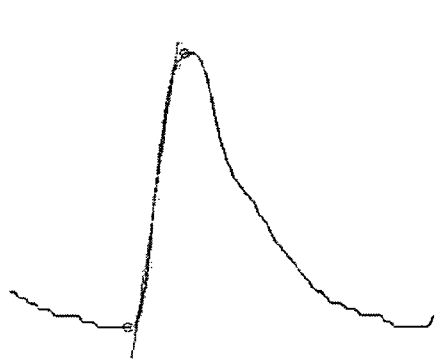
FIG. 2 is a sketch of pulse contours, with an interpolating linear function.
Figure 3:
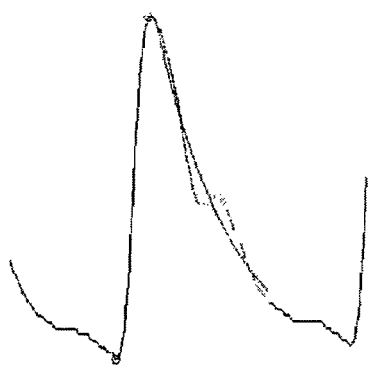
FIG. 3 is a sketch of pulse contours, with an exponential function.

Beat Validation: Evaluation of the Ascendant and Descendent Tracts of any Detected Beat Referring to FIGS. 2 and 3, showing a sketch of pulse contours, respectively with the interpolating linear function (FIG. 2) and exponential function (FIG. 3), it is useful to point out the following validation steps.

Step 1. Each detected beat is segmented into three sections.

Step 2. The similarity of the first section to a linear segment is evaluated using linear fitting. Similarity is quantified using the goodness of fit (R-squared) with a linear function (FIG. 2)

Step 3. The similarity of the third segment to an exponential decay is evaluated using and exponential fitting. Similarity is quantified using the goodness of fit (R-squared) with an exponential interpolating function (FIG. 3).

Step 4. If the R-squared of the linear and exponential tracts are both lower than a reference level, the beat is categorized as artifact.

Rational for Parameter Choice

Known parameters based on the morphological analysis of the ECG signal were excluded (e.g. P-wave detection). It is known that there are several parameters aimed to detect AF by analyzing the irregularity of the heart rhythm. Some of these parameters does not suit a short-term detection since they requires a relatively large number of beats, others require significant computational effort/memory occupation. Such methods have been excluded. Among the other known parameters a novel combination of two of them has been adopted, by empirical testing. Such peculiar combination has not been used previously. The performances of the proposed method have been verified on a population of 61 patients (43 with NSR, 14 with AF and 4 with other arrhythmias)

Details on Indexes Computation

Coefficient of variation is the ratio between the standard deviation for the series of the first derivatives of the beat-to-beat interval series ($\sigma\Delta PP$) and the mean value of the beat-to-beat interval series ($\mu PP$):

$$CV_{\Delta PP} = \frac{\sigma \Delta PP}{\mu PP}$$

where:

$$\mu PP = \frac{1}{N}\sum_{i=1}^{N} PP_i$$

: mean value of the beat-to-beat interval series $\sigma\Delta PP = \sqrt{((1)/N\Sigma\_(i=1)^N ⟦(⟦\Delta PP⟧\_i - ⟧\mu\Delta PP)⟧^2)}$: standard deviation of the series of the first derivatives of the beat-to-beat interval series $\mu\Delta PP = (1)/(N-1)\Sigma\_(i=1)^(N-1) ⟦\Delta PP\_i⟧$ : mean of the series of the first derivative of the beat-to-beat interval series $⟦\Delta PP⟧\_i = PP\_(i+1) - PP\_i$: series of the first derivatives of the beat-to-beat interval series $PP_i$: Interval between two consecutive beats N: Number of (consecutive) available beats Conventionally, CV of a temporal series is computed as the ratio between its standard deviation and its mean value. In this case, since the man value of the first derivatives of the beat-to-beat interval series ($\Delta PP$) is close to zero, the computation is made dividing for the mean value of the beat-to-beat interval series (PP).

The entropy is computed from the Shannon formula, that implies the estimation of the probability density function of the beat-to-beat interval series (by construction of the histogram).

$$EN_{PP} = -\sum_{k=1}^{M} p_k \ln(p_k)$$

where:

M=is the number of bins used to construct histogram $p_k$=is the probability of occurrence of a beat-to-beat interval, estimated as the ratio $n_k/N$, with $n_k$ representing the number of beat-to-beat intervals within the $k^{th}$ bin.

The bin amplitude have to be chosen sufficiently higher than the time resolution of the PP series, to obtain a reliable estimate of the histogram density, but not too large to avoid disruption of relevant information for the rhythm discrimination. The bin amplitude has been set to 16.6 ms.

Algorithm for Rhythm Classification

Rhythm classification is based on the measure of the distance of the couple of values CV and EN for a patient respect to the values characterizing a population of patients in atrial fibrillation and of subjects in sinus rhythm. Instead of the Euclidean distance, the Mahalanobis distance is used since it takes into account the parameters' dispersion within the population and their mutual correlation. Classification in NSR, AF or other arrhythmia is achieved by the following criteria:

If the Mahalanobis distance from the AF is lower than a properly selected value, rhythm is classified as AF, else if the Mahalanobis distance from NSR is lower than a properly selected value; rhythm is classified as Normal, else rhythm is classified as "Other Arrhythmia"

The properly selected values of the Mahalanobis distances have been chosen on the basis of the result from the clinical validation of the method.

From a set of values representative of a given population, the Mahalanobis distance is computed as $$D^2(x) = (x-\mu)^T S^{-1}(x-\mu)$$

Where:

x=set of parameters of the patient to be classified (CV and EN)

$\mu$=set of the mean value of the parameters in the reference population (sinus rhythm or atrial fibrillation) [$\mu CV$ $\mu EN$].

S=Covariance matrix, estimated on the parameters obtained from the reference population The formula becomes:

$$D_S^2(i) = [CV_i - \mu CV_S \quad EN_i - \mu EN_S]\begin{bmatrix} s_{1,1} & s_{1,2} \\ s_{2,1} & s_{2,2} \end{bmatrix}\begin{bmatrix} CV_i - \mu CV_S \\ EN_i - \mu EN_S \end{bmatrix}$$

$$D_{AF}^2(i) = [CV_i - \mu CV_{AF} \quad EN_i - \mu EN_{AF}]\begin{bmatrix} af_{1,1} & af_{1,2} \\ af_{2,1} & af_{2,2} \end{bmatrix}\begin{bmatrix} CV_i - \mu CV_{AF} \\ EN_i - \mu EN_{AF} \end{bmatrix}$$

where:

$D_S(i)$=distance of the patient i respect to the population in sinus rhythm $D_{AF}(i)$=distance of the patient i respect to the population in atrial fibrillation $\mu CV_S$=mean of parameter CV for the population of patients in sinus rhythm $\mu EN_S$=mean of parameter EN for the population of patients in sinus rhythm $\mu CV_{AF}$=mean of parameter CV for the population of patients in atrial fibrillaton $\mu EN_{AF}$=mean of parameter EN for the population of patients in atrial fibrillaton $$\begin{pmatrix} s_{1,1} & s_{1,2} \\ s_{2,1} & s_{2,2} \end{pmatrix}$$

coefficients of the inverse of covariance matrix, for the population in sinus rhythm $$\begin{pmatrix} af_{1,1} & af_{1,2} \\ af_{2,1} & af_{2,2} \end{pmatrix}$$

coefficients of the inverse of covariance matrix, for the population in atrial fibrillation Scientific Evidence/Clinical Validation The performances of the proposed method have been verified on a population of 61 patients with an history/suspect of AF. Heart Rhythm diagnosis was performed by an expert cardiologist, before each signal collection. 43 patients had NSR, 14 AF and 4 other arrhythmias.

A short-term pulseoximetric signal was collected at the finger, using a commercial pulseoximeter, which may have a connection with a laptop PC for signal storage and further analysis.

Beat validation showed high sensitive and specificity (>95%) in discriminating proper beats from artifacts.

The method classified correctly 43 out of 43 patient with Sinus Rhythm, 14 out of 14 patient with AF, 3 out of 4 patients with other arrhythmias. One patient with a supraventricular tachycardia was classified as normal sinus rhythm.

In terms of Sensitivity (Se) and Specificity (Sp) of AF detection, the method shows a Sp=100% and Se=100%. The accuracy was 98.4%.

REFERENCES

[1] Flaker G C, Belew K, Beckman K, Vidaillet H, Kron J, Safford R, Mickel M, Barrell P; AFFIRM Investigators. Asymptomatic atrial fibrillation: demographic features and prognostic information from the Atrial Fibrillation Follow-up Investigation of Rhythm Management (AFFIRM) study. Am Heart J. 2005 April; 149(4):657-63.

[2] Liao J, Khalid Z, Scallan C, Morillo C, O'Donnell M. Noninvasive cardiac monitoring for detecting paroxysmal atrial fibrillation or flutter after acute ischemic stroke: a systematic review. Stroke. 2007 November; 38(11):2935-40. Epub 2007 Sep. 27.

[3] Arya A, Piorkowski C, Sommer P, Kottkamp H, Hindricks G. Clinical implications of various follow up strategies after catheter ablation of atrial fibrillation. Pacing Clin Electrophysiol. 2007 April; 30(4):458-62.

[4] Tateno K, Glass L. Automatic detection of atrial fibrillation using the coefficient of variation and density histograms of RR and deltaRR intervals. Med Biol Eng Comput. 2001 November; 39(6):664-71.

[5] Duverney D, Gaspoz J M, Pichot V, Roche F, Brion R, Antoniadis A, Barthelemy J C. High accuracy of automatic detection of atrial fibrillation using wavelet transform of heart rate intervals. Pacing Clin Electrophysiol. 2002 April; 25(4 Pt 1):457-62.

[6] Esperer H D, Esperer C., Cohen R J. Cardiac Arrhythmias Imprint Specific Signatures on Lorenz Plots. Annals of Noninvasive. Electrocardiology 2008; 13(1):44-60.

[7] Hong-Wei L, Ying S, Min L, Pi-Ding L, Zheng Z. A probability density function method for detecting atrial fibrillation using R-R intervals. Med Eng Phys. 2009 January; 31(1):116-23. Epub 2008 Jun. 13

[8] Dash S, Chon K H, Lu S, Raeder E A. Automatic real time detection of atrial fibrillation. Ann Biomed Eng. 2009 September; 37(9):1701-9. Epub 2009 Jun. 17.

[9] Babaeizadeh S, Gregg R E, Helfenbein E D, Lindauer J M, Zhou S H. J Electrocardiol. 2009 November-December; 42(6):522-6. Epub 2009 Jul. 15. Improvements in atrial fibrillation detection for real-time monitoring.

[10] Park J, Lee S, Jeon M. Atrial fibrillation detection by heart rate variability in Poincare plot. *BioMedical Engineering OnLine* 2009, 8:38.

[11] Lu S, Zhao H, Ju K, Shin K, Lee M, Shelley K, Chon KH. Can photoplethysmography variability serve as an alternative approach to obtain heart rate variability information? J Clin Monit Comput. 2008 February; 22(1):23-9. Epub 2007 Nov. 7.

[12] Foo J Y, Wilson S J. Detection method to minimize variability in photoplethysmographic signals for timing-related measurement. J Med Eng Technol. 2006 March-April; 30(2):93-6

The invention claimed is:

1. A method for detection of an Atrial Fibrillation (AF) episode based on estimation of heart rhythm irregularity of a patient, said method comprising the following steps:
   a) obtaining a threshold pulse interval (PP) series by acquiring and processing a pulse plethysmographic waveform of a patient taken from a blood oxygenation device;
   b) analyzing said threshold pulse interval (PP) series; and
   c) measuring a set of patient features from the pulse plethysmographic waveform,
   wherein the set of patient features from the pulse plethysmographic waveform are a coefficient of variation (CV) of a dPP interval and a Shannon entropy value (EN) of a PP interval, analysis of heart rhythm comprising estimation of a Mahalanobis distance of said patient features from a reference population of patients in atrial fibrillation and of subjects in sinus rhythm.

2. A method according to claim 1 wherein the step a) comprises:
   I) estimation of a time-occurrence of each beat from a pulseoximetric waveform;
   II) construction of a beat-to-beat interval series;
   III) beat-validation to reduce artifacts through morphological analysis of ascendent and descendent tracts of a single pulse using a parametric modelling of a pulse waveform contour; and
   IV) removal of beat intervals with values shorter than 0.3 seconds and longer than 1.5 seconds.

3. A method according to claim 2, wherein each single pulse or heart beat in the single pulse plethysmographic waveform is segmented into three sections that comprises a first section, a second section, and a third section, the first section of the single pulse being compared to a linear segment, the third section of the single pulse being compared to an exponential decay tract, a similarity with linear and exponential function corresponding to said linear segment and decay being assessed using a goodness of R-squared fit.

4. A method according to claim 3, wherein the beat is categorized as an artifact and neglected if the R-squared fit of said linear segment and said exponential decay tract are both lower than a reference level.

5. A method according to claim 1 wherein in the step b), the Coefficient of variation is a ratio between a standard deviation for a series of first derivatives of the beat-to-beat interval series ($\sigma\Delta PP$) and a mean value of the beat-to-beat interval series while entropy is computed from a Shannon formula, that implies an estimation of a probability density function of the beat-to-beat interval series (by construction of a histogram), $$EN_{PP} = -\sum_{k=1}^{M} p_k \ln(p_k)$$

where:
M=is a number of bins used to construct the histogram, and
$p_k$=is a probability of occurrence of a beat-to-beat interval, estimated as a ratio $n_k/N$, with $n_k$ representing a number of beat-to-beat intervals within a $k^{th}$ bin.

6. A system to implement the method according to claim 1, said system being suitable to detect Atrial Fibrillation (AF) episodes based on estimation of a heart rhythm irregularity, the system comprising:
  a portable blood oxygenation monitoring device able to acquire at home a plethysmographic waveform of a patient over a period of time,
  means to storage in said device a computer program for processing said plethysmographic waveform,
  means to extract from said plethysmographic waveform two indexes, namely the Coefficient of variation (CV) of the dPP interval and a Shannon entropy (EN) of the PP interval, and
  means to evaluate the Mahalanobis distance of the patient parameters from the reference population of patients in atrial fibrillation and of subjects in sinus rhythm,
  wherein the means to extract from said plethysmographic waveform the two indexes and the means to evaluate the Mahalanobis distance are realized by a CPU configured to receive the plethysmographic waveform and configured to execute said computer program.

7. A system according to claim 6, further comprising display means with a three-state light indicator.

8. A system according to claim 6, further comprising means to detect artifacts, said artifacts being rejected.

9. A system according to claim 8, wherein said means to detect artifacts are the CPU, said CPU obtaining a pulse interval series from the plethysmographic waveform, the pulse interval series comprising a contour having three sections, a first section and a third section having forms which are respectively compared to a linear tract and to an exponential tract in order to detect the artifacts.

10. A system according to claim 6, wherein the CPU detects the Coefficient of variation according a ratio between a standard deviation for a series of first derivatives of a beat-to-beat interval series (σΔPP) and a mean value of the beat-to-beat interval series, said CPU computing an entropy from a Shannon formula, that implies an estimation of the probability density function of the beat-to-beat interval series (by construction of a histogram), $$EN_{PP} = -\sum_{k=1}^{M} p_k \ln(p_k)$$

where:
M=is a number of bins used to construct the histogram, and
$p_i$=is a probability of occurrence of a beat-to-beat interval, estimated as a ratio $n_k/N$, with $n_k$ representing a number of beat-to-beat intervals within a $k^{th}$ bin.

11. A system according to claim 7 wherein, the CPU is in a pulse oximeter.

* * * * *